(12) United States Patent
Babat et al.

(10) Patent No.: US 8,545,500 B2
(45) Date of Patent: Oct. 1, 2013

(54) BONE FIXATION ASSEMBLY

(75) Inventors: Brett Babat, Nashville, TN (US); John Kapitan, Waxhaw, NC (US); Martijn Heikens, Hengelo (NL); John J. Souza, Waxhaw, NC (US)

(73) Assignee: Omni Surgical LLC, Austin, TX (US)

( * ) Notice: Subject to any disclaimer, the term of this patent is extended or adjusted under 35 U.S.C. 154(b) by 271 days.

(21) Appl. No.: 12/998,289

(22) PCT Filed: Nov. 19, 2009

(86) PCT No.: PCT/US2009/065223
§ 371 (c)(1),
(2), (4) Date: Apr. 5, 2011

(87) PCT Pub. No.: WO2010/059881
PCT Pub. Date: May 27, 2010

(65) Prior Publication Data
US 2011/0208191 A1 Aug. 25, 2011

Related U.S. Application Data

(60) Provisional application No. 61/116,157, filed on Nov. 19, 2008.

(51) Int. Cl.
*A61B 17/56* (2006.01)
*A61B 17/58* (2006.01)
*A61B 17/80* (2006.01)
*A61F 2/30* (2006.01)

(52) U.S. Cl.
USPC ............... 606/71; 606/289; 606/328; 606/54

(58) Field of Classification Search
USPC .......... 606/54, 55, 59, 246, 104, 328, 71, 606/289, 290
See application file for complete search history.

(56) References Cited

U.S. PATENT DOCUMENTS

| | | | |
|---|---|---|---|
| 5,437,669 | A | 8/1995 | Yuan et al. |
| 5,620,443 | A | 4/1997 | Gertzbein et al. |
| 5,928,232 | A | 7/1999 | Howland et al. |
| 7,008,423 | B2 | 3/2006 | Assaker et al. |
| 7,344,537 | B1 | 3/2008 | Muller |
| 2004/0127900 | A1* | 7/2004 | Konieczynski et al. ........ 606/69 |
| 2006/0200146 | A1* | 9/2006 | Doubler et al. ................ 606/69 |

* cited by examiner

*Primary Examiner* — Andrew Yang
*Assistant Examiner* — Olivia C Chang
(74) *Attorney, Agent, or Firm* — David O. Simmons

(57) ABSTRACT

A fixation assembly and methods for its use are provided. The fixation assembly includes two or more fixation elements, at least one connection means adapted to engage with the fixation elements to connect them to one another, and a locking means that is actuated after engagement of the fixation elements with the connection means to simultaneously lock the fixation elements in place relative to one another and to the connection means.

19 Claims, 4 Drawing Sheets

BONE FIXATION ASSEMBLY

PRIORITY CLAIM

This application claims priority to International Patent Application No. PCT/US2009/065223, filed on Nov. 19, 2009, which claims priority to U.S. provisional patent application Ser. No. 61/116,157 filed on Nov. 19, 2008, the disclosures of both of which are hereby incorporated by reference, in their entireties, as if set forth fully herein.

BACKGROUND OF THE INVENTION

Bone fixation methods and assemblies are known in the art. Among the elements known in such methods and assemblies are screw locking mechanisms that include one or more bone screws and a fixation means (for example, another screw, a plate, or a flange) that engages with or extends over at least a portion of one or more bone screws to fix them in place.

The above notwithstanding, there remains a need in the art for effective bone fixation assemblies.

SUMMARY OF THE INVENTION

The present invention provides a fixation assembly that includes two or more fixation elements, at least one connection means adapted to engage with the fixation elements to connect them to one another, and a locking means that is actuated after engagement of the fixation elements with the connection means to simultaneously lock the fixation elements in place relative to one another and to the connection means. Each fixation element includes a securement means for securing the fixation element to a structure such as bone or another assembly or device and an attachment means for engaging the fixation element with the connection means. According to the various embodiments of the fixation assembly, the positions of the fixation elements can vary by one or both of lateral distance from one another and angulation relative to an axis defined by the connection means.

The present invention also provides methods for connecting and simultaneously locking together two or more fixation elements. According to the various embodiments, the methods involve securement of at least one of the fixation elements to a structure, such as a bone, prior to its engagement with a connector, followed by engagement of the secured fixation element with the connector, followed by actuation of a locking means to simultaneously lock the engaged fixation elements together with the connector. According to some embodiments, the methods involve the securement of two or more fixation elements, each secured to either the same or to different structures, prior to their engagement with a connector. According to other embodiments, the methods involve the engagement of the two or more fixation elements with the connector and the actuation of a locking means to simultaneously lock the engaged fixation elements together with the connector wherein at least one of the engaged and locked fixation elements is not secured to a structure.

BRIEF DESCRIPTION OF THE DRAWINGS

A more complete appreciation of the invention and the many embodiments thereof will be readily obtained as the same becomes better understood by reference to the following detailed description when considered in connection with the accompanying drawings, wherein.

DETAILED DESCRIPTION OF THE INVENTION

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

The present invention provides a fixation assembly that connects and locks together two or more fixation elements when a locking means is actuated. According to the various embodiments, the fixation assembly includes at least one connection means adapted to engage with the fixation elements to connect them to one another. The fixation assembly also includes two or more fixation elements, each comprising a securement means for securing the fixation element to a structure and an attachment means for engaging the fixation element with the connection means. And the fixation assembly includes a locking means that is actuated after engagement of the fixation elements with the connection means to simultaneously lock the fixation elements in place relative to one another and to the connection means.

The various embodiments of the disclosed fixation assembly are useful for connecting and locking together multiple fixation elements that include, for example, two or more bone screws that are secured in bone.

According to some uses, some embodiments of the disclosed fixation assembly are particularly useful where the bone screws are secured each to the same bone or to different bones and are oriented along axes that are not parallel, i.e., their angulation varies relative to a selected axis. Thus, where two or more bone screws are secured to bone along different axes or trajectories, some embodiments of the disclosed fixation assembly are adapted to engage with each of these polyaxially oriented screws to effectively connect and lock them with a connector using a single remote locking means. According to some such embodiments, the connector may be further connected with another structure, assembly or device via a fixation element that is not connected directly to bone, such as for example, a rod that is suitable for engagement with two or more of a series of devices such as one or a combination of fixation assemblies according to this disclosure and known bone anchor or attachment devices already known in the art. As an example, using the connection means for engaging with one or more bone screws placed in the pelvis, the secured screws may be connected to a rod that is part of a spinal construct, thereby linking and locking the spinal construct to the pelvis, wherein the rod is engaged with the fixation assembly as a fixation element according to one or more of the embodiments herein described.

According to other uses, embodiments of the disclosed fixation assembly are useful where the bone screws are secured each to the same or to different bones and may be separated by a variable distance. According to such embodiments, the connection means is a connector that has movable portions that can be adjusted so as to engage with each of the secured fixation elements and then locked into place upon actuation of the locking means. As an example, for a variety of instances where connection of fixation elements is desirable across a lumbar, thoracic, or cervical disc space to be fused, or across a larger gap created by bone resection (e.g. a corpectomy defect), combinations of fixation elements may be used and connected together using one or a series of fixation assemblies according to the instant invention. Thus, for example, two screws may be positioned within bone on one side of a gap or disc space and connected with a connection means such as a rod or plate and then interconnected across the space to another one or more fixation assembly via connection means components or one or more fixation elements that engage with structures other than bone.

According to yet other uses, embodiments of the disclosed fixation assembly are useful where the bone screws are secured the same bone or to different bones and are oriented along axes that are not parallel and may be separated by either or both a variable lateral or vertical distance. Thus, according to such embodiments, the fixation assembly is adapted to accommodate polyaxially oriented screws and to adjust to accommodate screws that are spaced at other than fixed distances from one another. In one possible use of such embodiments two or more screws converging or diverging in one or more planes may be placed in the iliac wing and then locked together.

In some representative embodiments as further described herein, the bone fixation assembly includes, but is not limited to, a connector adapted with a receiving bore to engage one or a plurality of fixation elements, fixation elements may be selected from, for example, bone screws, connecting rods, posts, loops, hooks, and combinations of these, and a locking means that includes for example, a conical screw or nut, a twist lock screw or nut, a cam mechanism, or a snap fit nut, that is adapted to engage with the connector. According to such embodiments, upon engagement of all of the fixation elements with the connector, the locking means is actuated to connect and lock the assembly.

In some embodiments the connector may also include components adapted for engagement with one or more structures and may comprise engagement elements selected from threaded receivers, acceptors, connecting rods, posts, loops, hooks, and combinations of these. Actuation of the locking means displaces locking elements selected from one or a combination of friction blocks and flexors toward and against the fixation elements to effectively lock the fixation elements relative to the connector and to each other.

It will be appreciated that the material selected for any fixation assembly component will have acceptable compatibility for its use, such as biocompatibility, and may be selected from a wide variety of metal, non metal and combinations of these that are known in the art. It will also be appreciated that with respect to the various components there may be a variety of fasteners and connectors between them, including rods, blockers, rods with one or more eyelets, spheres, threaded, tapered or cylindrical feature, that mate with other components and other fastener types as described herein. And it will be appreciated that various components may be made as unitary or monolithic structures or they may be multipart components that are connected to one another by a variety of means. Thus, except as specifically described herein with respect to the engagement between the connection means, fixation elements and locking means, subcomponents of these may be made in unitary, multi component forms that may be connected by a variety of means and may be made of one or a combination of suitable materials.

Figure 1:
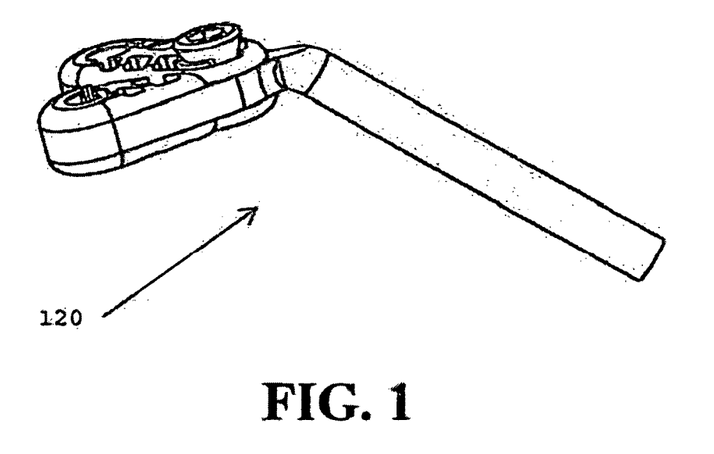
FIG. 1 illustrates a portion of an embodiment of a fixation assembly that includes a connector and a locking means that includes a conical nut.
Figure 2:
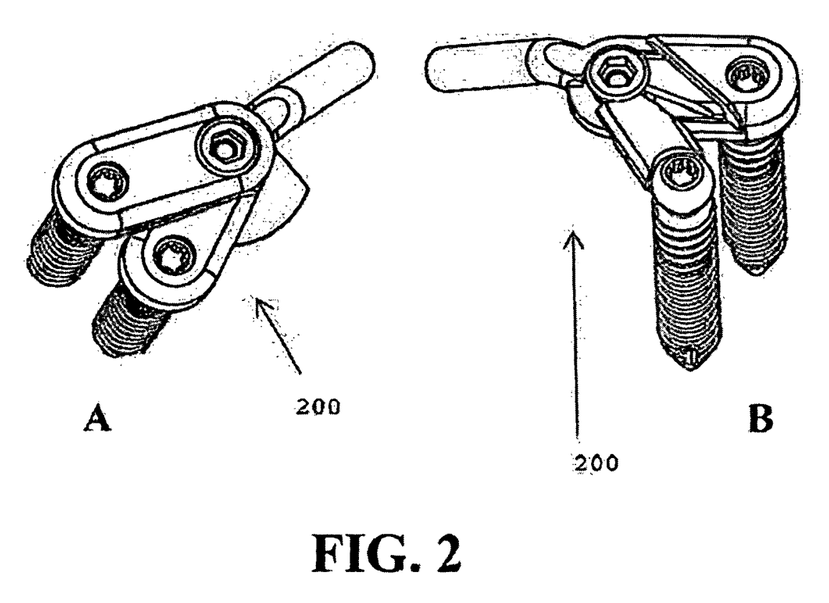
FIG. 2 illustrates a different embodiment of a fixation assembly that includes a connector a locking means that includes a conical nut and two fixation elements.

Referring now to FIG. 2, one embodiments of a fixation assembly 200 is depicted wherein each of the components is shown engaged with the others. Referring now to FIG. 5, another embodiment of a fixation assembly 300 is depicted wherein each of the components is shown in panel A engaged with the others and in panel B disengaged from the others. In this depicted embodiment, the connection means is a connector 320 in the form of a planar plate having three fixed and radially oriented equally spaced apart blades or arms. The depicted embodiment also includes three fixation elements including two screws 340 and one rod 360. In the depicted embodiment, the locking means includes a threaded and conical nut 380. FIGS. 1-4 and 6 depict alternate embodiments of fixation assemblies, each showing varied examples of the connection means, locking means and fixation elements, as more fully described herein.

Figure 4:
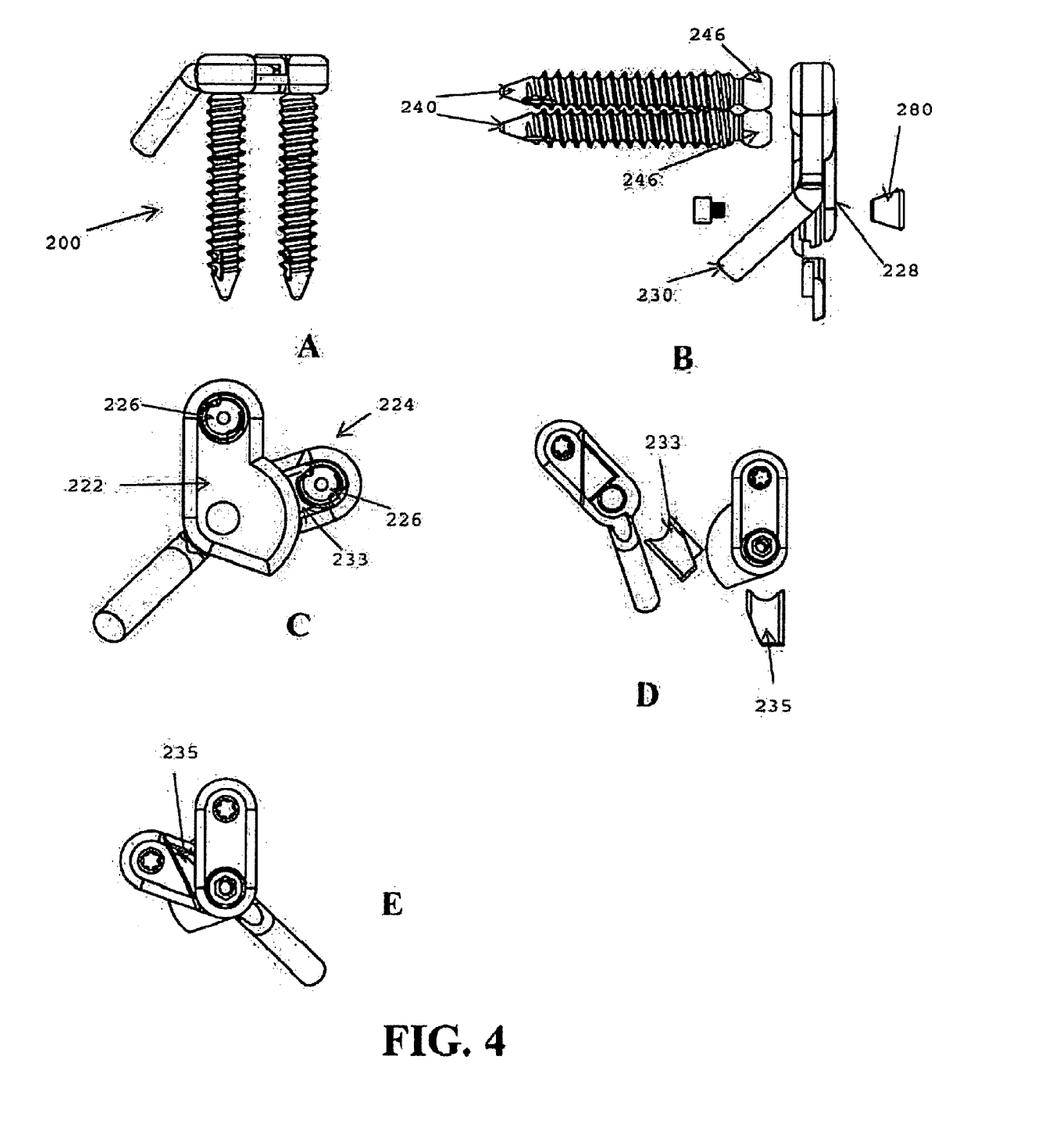
FIG. 4 illustrates views of the fixation assembly shown in FIG. 2, wherein panels A and B show alternate side plan view of the assembly, panel C shows a bottom plan view, panel E shows a top plan view, and panel D shows a cut away top plan view of the two blades of the connector revealing the locking elements.
Figure 5:
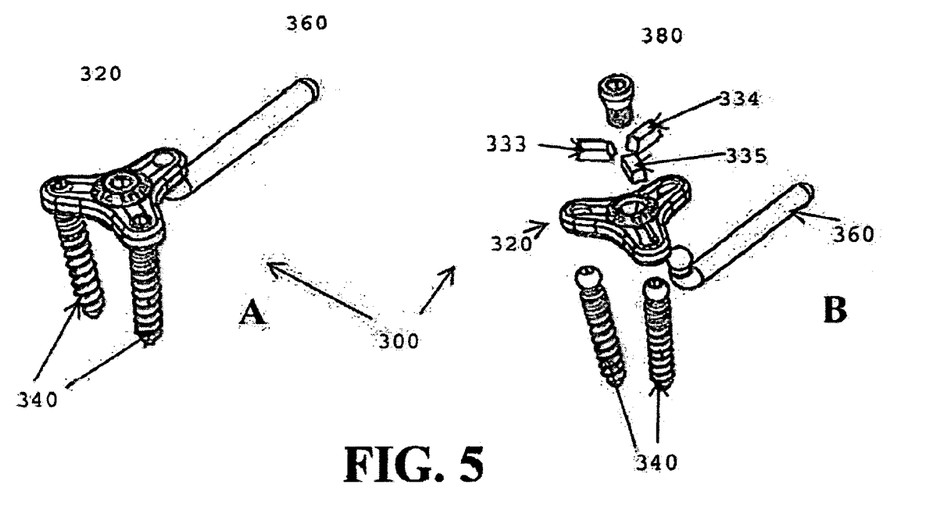
FIG. 5 illustrates in panels A and B engaged and blown apart views of yet a different embodiment of the fixation assembly, panel B showing the detail of the threaded conical nut and locking elements 3333, 334, and 335 of the locking means above the connector and the rod and screw fixation elements.

Referring now to FIG. 4, the depicted connector 220 includes a pair of substantially planar blades 222 and 224 and a post component 230 suitable for engagement or attachment with another device or structure. Each of the planar blades 222 and 224 is adapted for engagement with an attachment means of a fixation element. As depicted, the attachment means of each of the fixation elements 240 is a substantially spherical head 246 that is attached through a bore 226 in the connector 220. The bore 226 is sized to accommodate the spherical head 246 and allows it to rotate within the bore 226 such that the axial position of the fixation element 240 varies relative to the axis of the bore 226. According to this depicted embodiment, the connector 220 is adapted to accommodate two attached fixation elements 240 in varied orientations relative to one another, and allows adjustment of the position of the connector so as to engage with each of the fixation elements 240 and then fix its position relative to the fixation elements 240 upon actuation of the locking means. As depicted, the connector 220 includes a locking seat 228 for receiving the locking means, depicted as a conical nut 280, and locking elements 233 and 235 which are in operative communication with the locking seat 228, whereby, upon engagement of the threaded conical nut 280 in the locking seat 228 the locking elements 233 and 235 are displaced into contact with the attachment means 246 of the fixation elements 240 to lock the fixation assembly 200.

Figure 3:
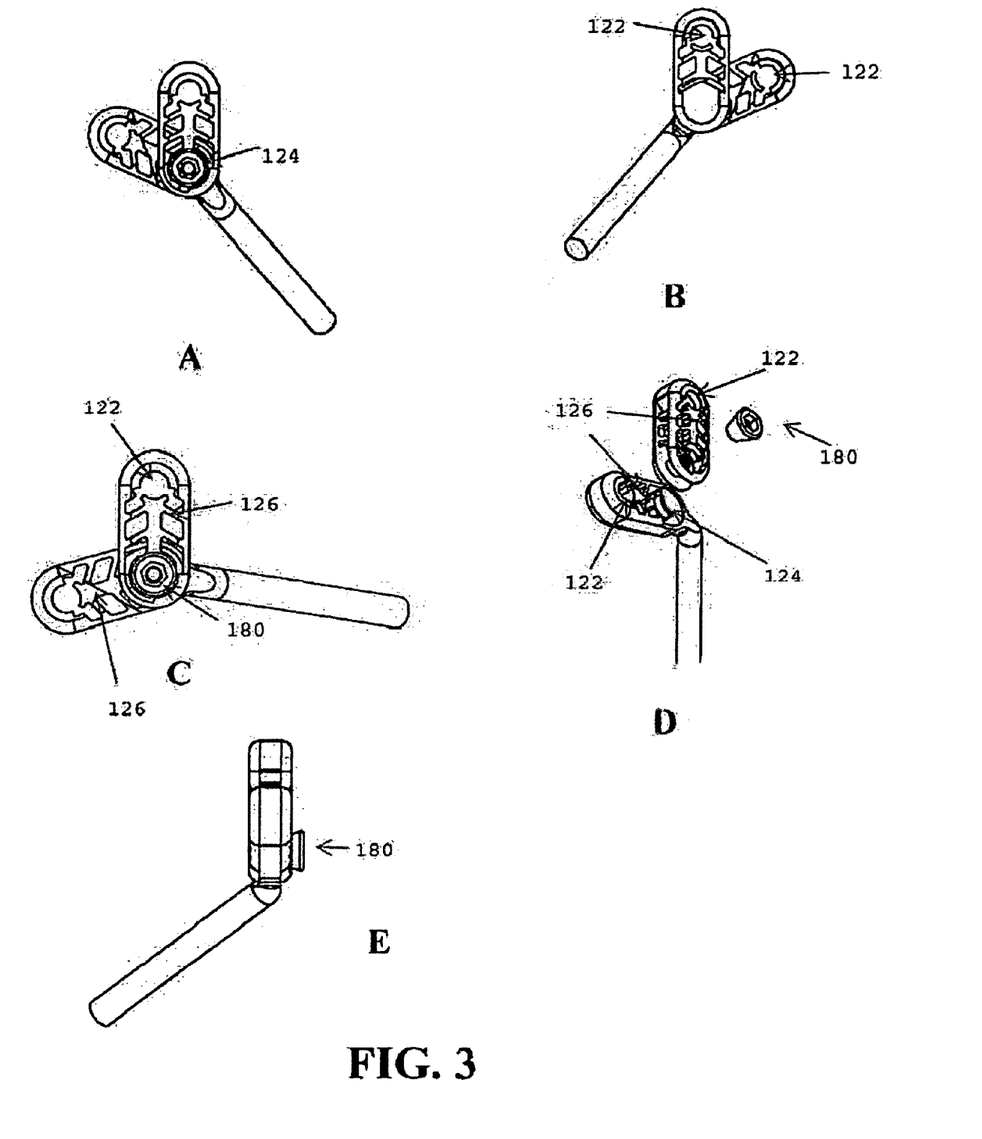
FIG. 3 illustrates views of the portion of the fixation assembly shown in FIG. 1, wherein panels A, B and C show opposite top and bottom views of the connector, panel D shows a perspective view with the blades of the connector and the conical nut disengaged, and panel E shows a side plan view of the connector.

The locking elements 233 and 235 as depicted in FIG. 4 are movable components that are formed with the connector and move within a channel between the locking seat and the bore for receiving a fixation element. According to this embodiment, actuation of the locking means by insertion of the conical nut into the locking seat displaces the locking elements toward and into contact with the attachment means of the fixation elements to lock the fixation assembly. In alternate embodiments, as depicted in FIG. 1 and FIG. 3, the locking elements 126 are immobile elements that are integral with or integrated with the connector and have a open web or lattice form. According to this embodiment, actuation of the locking means by insertion of the conical nut 180 into the locking seat 124 deforms the locking elements 126, displacing them toward and into contact with the attachment means of the fixation elements 140 and 160 to lock the fixation assembly 100.

It will be appreciated that according to alternate embodiments, a connector may have a different form that is not a plate. As an example, the connecting element may be a rod or a plate that tapers into a rod. It will also be appreciated that a connector need not be substantially planar, and may have an arcuate shape or a wave shape, or a combination of planar and arcuate portions, wherein an arcuate connector or connector portion may have radius of curvature that is suitable for a selected use, such as for connection of multiple fixation elements along an anatomical structure that is curved and may curve or angle in more than one plane. While the various embodiments of the connector are shown to have arm like extensions, these are not intended to be limiting. The shapes, lengths and orientations of the portions of a connector which engage with each fixation element may vary.

The adaptation for engagement with a fixation element may also vary. For example, according to embodiments having a bore for receiving a fixation element, the bore may have an internal surface that has a cylindrical, spherical, conical, hexagonal, pentagonal or other polygonal shape. In some embodiments the shapes of the bore surface and of the attachment means of a fixation element are complimentary and in other embodiments they are not. In some examples, the bore may be adapted with at least one collet or bushing that may be continuous or that is partially or fully slit. Thus, it will be appreciated that variations in the bore will influence the adjustability of the position of the attachment means of a fixation element relative to the connector.

It will be appreciated that he shape and configuration of the locking elements may vary. Thus, while the depicted locking elements are essentially rectangular in shape, they may have other shapes that more closely conform to the shape of the connector or connector arm in which they are positioned, or they may be cylindrical in shape or may be non conforming. In some examples, locking elements may be formed of a material that is the same as the material of the connector, while in other embodiments locking elements may be formed of a different material.

Thus, for example, in some embodiments, the connector may be formed of a suitable material selected from metal, metal alloy and composite, and a locking element is formed of the same material and is either of separate or unitary construction with the connector. In other embodiments, the connector may be formed of a suitable material selected from metal, metal alloy and composite and the locking element is formed of a different material, which may be more compressible and deformable as compared with the connector material. In one example, one or more locking element may be formed with an elastomeric material such as a rubber. In some embodiments, that the material will have sufficient resiliency to recover from deformation upon removal of the locking force and to tolerate the strain of deformation without breach or failure. In yet other embodiments the material will be permanently deformable. Materials having a variety of resiliency and deformation resistant properties are known in the art, and it will be appreciated that the selection of material can be achieved according to skills well known in the art for providing the desired properties that will influence overall resiliency, flexibility, rigidity, strength, durability, and the like.

Referring again to FIG. 4, the connector 220 has two blades that are movable relative to each other, wherein a first blade 224 is shown attached to the connector rod 230 and provides the axis around with the second blade 224 pivots. As depicted, the movement of the blades is pivotal around an axis that also defines the locking seat 224. It will be appreciated that in other embodiments, the connector blades may be fixed relative to one another, or they may both be movable around an axis. And in yet other embodiments, connectors may have more than two blades and the blades may move differently such at least one is pivotal or rotatable. In other embodiments, a connector may have three or more arms, wherein all of the arms are movable relative to the other or wherein fewer than all the arms are movable.

Figure 6:
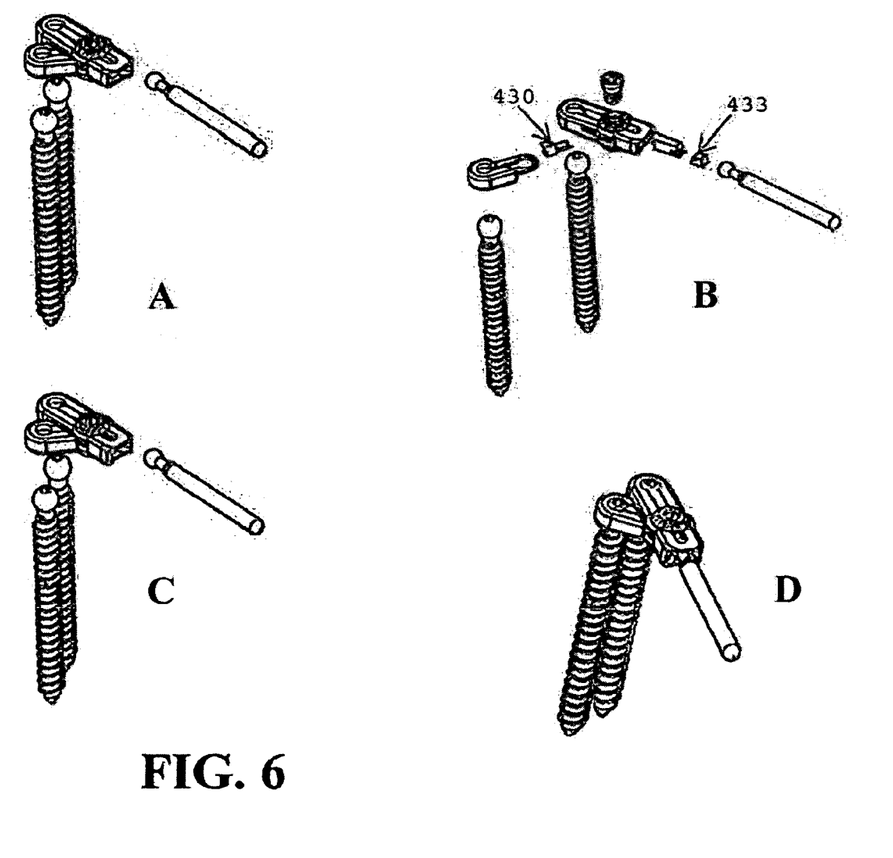
FIG. 6 illustrates in panels A through D a progression of views from blown apart to engaged components of yet a different embodiment of the fixation assembly, panel B showing the detail of the threaded conical nut and locking elements 433 and 435 of the locking means by the connector and the rod fixation element and above the screw fixation elements.

FIG. 3 and FIG. 6 show other embodiments wherein the depicted connectors also have arms or blades that are movable. According to these various embodiments, the connector can be adjusted so as to accommodate two or more secured fixation elements that are separated from one another at one or more of a variable lateral or vertical distance. In some examples, a series of two or more connectors can be interconnected through attachment between fixation elements or other intermediate devices to enable engagement of three or more secured fixation elements that are not on the same plane, wherein each such connector is part of a separate fixation assembly that operates independently from the other fixation assembly or assemblies.

Fixation elements include bone screws, rods, posts, or other elements that can be engaged with a structure such as bone or a device. According to the various embodiments, each fixation element includes a securement means for securing the fixation element to a structure, such as bone or other assemblies or devices. In some embodiments, the securement means is a threaded portion that is suitable for engagement with bone, or with a complementary threaded device. In other embodiments, the securement means is selected from a post, rod, loop, hook or other structure, and may be smooth, threaded, have one or multiple beads or bores that facilitate engagement with a structure.

According to the various embodiments, each fixation element also includes an attachment means for engaging the fixation element with a connection means. The attachment means may have a substantially spherical shape as shown in the various figures. In alternate embodiments (not shown) the attachment means may have a different shape that is selected from cylindrical, spherical, conical, hexagonal, pentagonal and other polygonal shapes. The shape of the attachment means may be complimentary with the portion of the connector that engages with it, or they may have non-complimentary shapes. In some embodiments the surface of either or both the connector engagement, such as a bore, and the attachment means may be textured or patterned to enhance the contact between their surfaces when the locking means is actuated so as to enhance resistance to slippage.

Thus, in some embodiments, fixation elements include any of a variety of bone screws that are know in the art and employed or useful for a variety of bone attachment applications. In some examples, a fixation element is a bone screw having a threaded portion suitable for engagement with bone. In other examples, a fixation element is a hook, wire, or cable suitable for engagement with bone. In yet other examples, the fixation element is an attachment structure that is capable of engagement with another device or structure. For instance, in some embodiments, the fixation elements are rods or other extended structures that are suitable for attachment to additional assemblies or devices. In other embodiments, fixation elements may include cages of varying geometry and material. And in yet other embodiments, the fixation elements are posts, or other elements that can have varied shapes, such as loops, or hooks or cables.

The locking means includes a component that engages with the connector to fixedly engage the fixation elements to the assembly. In various embodiments, the locking means comprises a component such as a rivet, screw, nut, bolt, clip, clamp, twist lock screw or nut, cam mechanism, or snap fit nut. Referring to the fixation assembly depicted in FIG. 1 and FIG. 3 as an example, the depicted locking means component is a conical nut 180 that engages in the locking seat 124 and is secured to the connector 120 via an externally threaded post (not shown) that engages with complementary threads within an internal bore (not shown) in the conical nut 180. In yet other similar embodiments, referring now to FIG. 5 and FIG. 6, the depicted locking means component is a threaded conical nut. Referring now to FIG. 3, the conical shape of the nut 180 contacts with locking elements 126 as the nut 180 is inserted into the locking seat 124 and displaces them to achieve contact and locking with the fixation elements once the nut is locked to the connector via the threaded post. In some embodiments, the nut may be permanently locked, while in other embodiments it may be disengaged to unlock the assembly.

Of course it will be appreciated that the locking means as depicted in the described figure is but one possible locking means useful according to the instant invention. In some embodiments, a locking means is a fastener selected from a variety of fasteners know in the art, including rivets, screws, nuts, bolts, clips, clamps, twist lock screw or nut, a cam mechanism, or a snap fit nut, wherein the fastener operates by engagement with a structure other than locking elements as described herein. For example, a locking means may include simply a nut that engages with a bolt or other treaded post type structure to engage and fix together a connector and one or more movable components, or such locking means may engage directly with the attachment means of a fixation element that is engaged with a connector so as to achieve locking of that fixation element to the connector.

It will be appreciated that other shapes and configurations of the locking component are possible, and can include any one or more of such elements to achieve locking by threaded, snap fit, and cam mechanisms. The shape may be selected from cylindrical, spherical, conical, hexagonal, pentagonal and other polygonal shapes, and the shape of the locking seat 124 may be complimentary with or different from this shape. The lock actuating feature may also vary, such that rather than the shape of the locking component causing displacement of locking elements, the component may include on or more of flanges, ridges or other features that engage with the connector and or the locking elements to cause displacement of the elements for engagement with the fixation elements.

Thus, in some embodiments there is a connector and a single locking means and a single fixation element. In some other embodiments there is a connector and a single locking means and a plurality of fixation elements each of which may be the same or different from one another. And in yet other embodiments there is a connector and two or more locking means and a plurality of fixation elements each of which may be the same or different from one another, wherein each of the locking means operates to lock the connector to at least one of the plurality of fixation elements and wherein each of the two or more locking means may lock only one fixation element or multiple fixation elements to the connector. In yet other embodiments, one or more connector components may be present and may be fixed or movable relative to the connector prior to locking such that in some such embodiments, upon actuation of one of the locking means a movable connector component may be locked into position relative to the fixation assembly. An example of such an embodiment is a flange, rod or wing that is rotatable around an element of the connector and is fixed to the connector by a locking means selected from a screw, nut, bolt, clamp, snap or other In accordance with the foregoing, numerous alternate embodiments of the fixation assembly are possible to enable the connection and locking of various discrete fixation elements. The present invention should not be considered limited to the specific embodiments and examples described herein, but rather should be understood to cover all aspects of the invention. Various modifications, equivalent processes, structures and devices to which the present invention may be applicable will be readily apparent to those of skill in the art.

We claim:

1. A bone fixation assembly, comprising:
a connector including a plurality of fixation element engaging blades each configured for being engaged with the attachment means of a respective one of a plurality of fixation elements, wherein a first one the fixation element engaging blades is moveably attached to a second one of the fixation element engaging blades for allowing a relative orientation of an attachment means engaging portion of the first one the fixation element engaging blades and an attachment means engaging portion of the second one the fixation element engaging blades to be altered and wherein the attachment means engaging portion of each one of the fixation element engaging blades is adapted to be engaged with the attachment means of the respective one of the fixation elements after the securement means of the respective one of the fixation elements is secured to the structure, and
a locking means mounted jointly on the fixation element engaging blades, wherein the locking means is adapted to be actuated after engagement of the fixation element engaging portion of each one of the fixation element engaging blades with the attachment means of the respective one of the fixation elements to secure the fixation element engaging blades to the attachment means of the respective one of the fixation elements and thereby secure the fixation element engaging blades in place relative to one another.

2. The fixation assembly according to claim 1 wherein the attachment means engaging portion of each one the fixation element engaging blades includes a bore configured to accommodate a spherical head of the respective one of the fixation elements in a manner allowing a position at which the fixation elements are secured to a structure to be varied relative to lateral distance from one another and relative to angulation relative to each other.

3. The fixation assembly according to claim 2 wherein:
the attachment means engaging portion of each one of the fixation element engaging blades is at a first end portion thereof; and
a second end portion of the first one the fixation element engaging blades is pivotably attached to a second end portion of the second one of the fixation element engaging blades for allowing a distance between the attachment means engaging portion of the first one the fixation element engaging blades and the attachment means engaging portion of the second one the fixation element engaging blades to be altered.

4. The fixation assembly according to claim 1 wherein:
the attachment means engaging portion of each one of the fixation element engaging blades is at a first end portion thereof; and
a second end portion of the first one the fixation element engaging blades is pivotably attached to a second end portion of the second one of the fixation element engaging blades for allowing a distance between the attachment means engaging portion of the first one the fixation element engaging blades and the attachment means engaging portion of the second one the fixation element engaging blades to be altered.

5. The fixation assembly according to claim 1 wherein:
the locking means includes a plurality of locking elements and a locking element actuator;
each one of the locking elements is slideably mounted within a channel of a respective one of the fixation element engaging blades; and
movement of the locking element actuator from a first position to a second position causes each one of the locking elements to slide within the channel of the respective one of the fixation element engaging blades such that an attachment means contacting portion of each one of the locking elements enters the bore of the respective one of the fixation element engaging blades.

6. The fixation assembly according to claim 5 wherein:
each one of the locking elements includes a ramped edge face; and
the locking element actuator includes a ramped side surface such that engagement of the ramped side surface of the locking element actuator with the ramped edge face of each one of the locking elements when the locking element actuator is being moved from the first position to the second position results in each one of the locking elements sliding within the channel of the respective one of the fixation element engaging blades such that each one of the locking elements move toward the bore of the respective one of the fixation element engaging blades.

7. A fixation assembly component system, comprising:
a plurality of fixation elements, each one of the fixation elements comprising a securement means for securing the fixation element to a structure and an attachment means,
a connection means including a plurality of fixation element engaging blades each configured for being engaged with the attachment means of a respective one of the fixation elements, wherein a first one the fixation element engaging blades is moveably attached to a second one of the fixation element engaging blades for allowing a relative orientation of an attachment means engaging portion of the first one the fixation element engaging blades and an attachment means engaging portion of the second one the fixation element engaging blades to be altered and wherein the attachment means engaging portion of each one of the fixation element engaging blades is adapted to be engaged with the attachment means of the respective one of the fixation elements after the securement means of the respective one of the fixation elements is secured to the structure, and
a locking means mounted jointly on the fixation element engaging blades, wherein the locking means is adapted to be actuated after engagement of the fixation element engaging portion of each one of the fixation element engaging blades with the attachment means of the respective one of the fixation elements to secure the fixation element engaging blades to the attachment means of the respective one of the fixation elements and thereby securing the fixation element engaging blades in place relative to one another.

8. The fixation assembly component system according to claim 7, wherein the first one the fixation element engaging blades is pivotably attached to the second one of the fixation element engaging blades for allowing a distance between the attachment means engaging portion of the first one the fixation element engaging blades and the attachment means engaging portion of the second one the fixation element engaging blades to be altered.

9. The fixation assembly component system according to claim 8 wherein:
the attachment means of each of the fixation elements includes a substantially spherical head; and
the attachment means engaging portion of each one the fixation element engaging blades includes a bore configured to accommodate the spherical head of the respective one of the fixation elements in a manner allowing a position at which the fixation elements are secured to the structure to be varied relative to lateral distance from one another and relative to angulation relative to each other.

10. The fixation assembly component system according to claim 7 wherein:
the attachment means of each of the fixation elements includes a substantially spherical head; and
the attachment means engaging portion of each one the fixation element engaging blades includes a bore configured to accommodate the spherical head of the respective one of the fixation elements in a manner allowing a position at which the fixation elements are secured to the structure to be varied relative to lateral distance from one another and relative to angulation relative to each other.

11. The fixation assembly component system according to claim 7 wherein:
the attachment means engaging portion of each one of the fixation element engaging blades is at a first end portion thereof; and
a second end portion of the first one the fixation element engaging blades is pivotably attached to a second end portion of the second one of the fixation element engaging blades for allowing a distance between the attachment means engaging portion of the first one the fixation element engaging blades and the attachment means engaging portion of the second one the fixation element engaging blades to be altered.

12. The fixation assembly component system according to claim 9 wherein:
the attachment means engaging portion of each one of the fixation element engaging blades is at a first end portion thereof; and
a second end portion of the first one the fixation element engaging blades is pivotably attached to a second end portion of the second one of the fixation element engaging blades for allowing a distance between the attachment means engaging portion of the first one the fixation element engaging blades and the attachment means engaging portion of the second one the fixation element engaging blades to be altered.

13. The fixation assembly component system according to claim 10 wherein:
the attachment means engaging portion of each one of the fixation element engaging blades is at a first end portion thereof; and
a second end portion of the first one the fixation element engaging blades is pivotably attached to a second end portion of the second one of the fixation element engaging blades for allowing a distance between the attachment means engaging portion of the first one the fixation element engaging blades and the attachment means engaging portion of the second one the fixation element engaging blades to be altered.

14. The fixation assembly component system according to claim 7 wherein:
the attachment means of each of the fixation elements includes a substantially spherical head;
the attachment means engaging portion of each one of the fixation element engaging blades is at a first end portion thereof;
the attachment means engaging portion of each one the fixation element engaging blades includes a bore configured to accommodate the spherical head of the respective one of the fixation elements in a manner allowing a position at which the fixation elements are secured to the structure to be varied relative to lateral distance from one another and relative to angulation relative to each other;
a second end portion of the first one the fixation element engaging blades is pivotably attached to a second end portion of the second one of the fixation element engaging blades for allowing a distance between the attachment means engaging portion of the first one the fixation element engaging blades and the attachment means engaging portion of the second one the fixation element engaging blades to be altered;
the locking means includes a plurality of locking elements and a locking element actuator;
each one of the locking elements is slideably mounted within a channel of a respective one of the fixation element engaging blades; and
movement of the locking element actuator from a first position to a second position causes each one of the locking elements to slide within the channel of the respective one of the fixation element engaging blades such that an attachment means contacting portion of each one of the locking elements enters the bore of the respective one of the fixation element engaging blades.

15. The fixation assembly component system according to claim 14 wherein:
each one of the locking elements includes a ramped edge face; and
the locking element actuator includes a ramped side surface such that engagement of the ramped side surface of the locking element actuator with the ramped edge face of each one of the locking elements when the locking element actuator is being moved from the first position to the second position results in each one of the locking elements sliding within the channel of the respective one of the fixation element engaging blades such that each one of the locking elements move toward the bore of the respective one of the fixation element engaging blades.

16. A bone fixation assembly component system comprising:
a plurality of fixation elements that each comprise a bone screw comprising a securement means for securing the fixation element to bone and an attachment means,
a connector including a plurality of fixation element engaging blades each being adapted to engage with the attachment means of the bone screw of a respective one of the fixation elements, and
a locking means mounted jointly on the connector, wherein the locking means is adapted to be actuated after engagement of the bone screw of the respective one of the fixation elements with the fixation element engaging blades of the connector to lock the bone screws in place relative to the connector,
wherein, the locking means comprises a plurality of locking elements that are each moveably mounted on a respective one of the fixation element engaging blades, and a locking nut that is adapted for engagement in a receiving portion of the connector such that the nut, when engaged with the connector, contacts the each one of the locking elements so as to displace each one of the locking elements toward and into contact with the attachment means of the bone screw of the respective one of the fixation elements.

17. The bone fixation assembly component system of claim 16, wherein the attachment means is a substantially spherical screw head that engages with a bore in the connector, and wherein the securement means is at least one screw thread.

18. The bone fixation assembly component system of claim 16 wherein:
the connector includes a first fixation element engaging blade and a second fixation element engaging blade;
the first fixation element engaging blade is pivotably attached to the second fixation element engaging blade for allowing a relative orientation of an attachment means engaging portion of the first one the fixation element engaging blades and an attachment means engaging portion of the second one the fixation element engaging blades to be altered; and
each one of the locking elements is slideably mounted within a channel of a respective one of the fixation element engaging blades.

19. The bone fixation assembly component system of claim 18 wherein:
- each one of the locking elements includes a ramped edge face; and
- the locking nut includes a ramped side surface such that engagement of the ramped side surface of the locking nut with the ramped edge face of each one of the locking elements when the locking nut is engaged with the connector results in each one of the locking elements sliding within the channel of the respective one of the fixation element engaging blades such that each one of the locking elements move toward the bore of the respective one of the fixation element engaging blades.

\* \* \* \* \*